(12) United States Patent
Zushi

(10) Patent No.: US 10,539,462 B2
(45) Date of Patent: Jan. 21, 2020

(54) ANALYSIS SYSTEM AND OPTICAL ELEMENT REPLACEMENT TIMING DETERMINATION METHOD

(71) Applicant: SHIMADZU CORPORATION, Kyoto (JP)

(72) Inventor: Jumpei Zushi, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 0 days.

(21) Appl. No.: 16/160,304

(22) Filed: Oct. 15, 2018

(65) Prior Publication Data

US 2019/0120690 A1    Apr. 25, 2019

(30) Foreign Application Priority Data

Oct. 19, 2017    (JP) .................. 2017-202489

(51) Int. Cl.
*G01J 3/42*    (2006.01)
*G01J 3/28*    (2006.01)
(Continued)

(52) U.S. Cl.
CPC ............. *G01J 3/2803* (2013.01); *G01J 3/027* (2013.01); *G01J 3/10* (2013.01); *G01J 3/42* (2013.01); *G01N 21/15* (2013.01); *G01J 2003/106* (2013.01); *G01N 2021/157* (2013.01); *G01N 2201/127* (2013.01)

(58) Field of Classification Search
CPC .... G01J 3/2803; G01J 3/42; G01J 3/10; G01J 3/027; G01J 2003/106; G01N 21/15; G01N 2201/127; G01N 2021/157; F21V 5/04; F21V 15/01; F21V 23/02; G06Q 10/00
See application file for complete search history.

(56) References Cited

U.S. PATENT DOCUMENTS

| 2010/0171049 A1 | 7/2010 | Moriya et al. |
| 2012/0038925 A1 | 2/2012 | Gahr et al. |
| 2016/0208998 A1* | 7/2016 | Greinke ................. F21S 8/061 |

FOREIGN PATENT DOCUMENTS

| JP | 2001-317997 | 11/2001 |
| JP | 2002-296284 | 10/2002 |
| JP | 2012-242276 | 12/2012 |

OTHER PUBLICATIONS

EP 18200934.0, Extended European Search Report, dated Mar. 1, 2019, 9 pages—English.

* cited by examiner

*Primary Examiner* — Abdullahi Nur
(74) *Attorney, Agent, or Firm* — Andrew F. Young, Esq.; Lackenbach Siegel, LLP

(57) ABSTRACT

An analysis system 10 includes a plurality of spectrophotometers 1, a memory storage 11, and a control terminal 12. The spectrophotometer 1 further includes a light source 2, a light detector, and an optical element that introduces light from the light source 2 to the light detector. The memory device 11 stores the information as the control information 110 relative to the light amount of the light detected by the light detector 6 right after replacement when replacing the light source of the spectrophotometer 1. A replacement timing determination unit 125 of the control terminal 12 reads out a control information 110 in the memory device 11 and determines the replacement timing of the optical element based on the value of the light amount information of the read-out control information 110.

7 Claims, 6 Drawing Sheets

(51) Int. Cl.
*G01J 3/02* (2006.01)
*G01N 21/15* (2006.01)
*G01J 3/10* (2006.01)

ANALYSIS SYSTEM AND OPTICAL ELEMENT REPLACEMENT TIMING DETERMINATION METHOD

CROSS REFERENCE TO RELATED APPLICATIONS

This application relates to, and claims priority from, Ser. No. JP2017-202489 filed on Oct. 19, 2017, the entire contents of which are incorporated herein by reference.

FIGURE SELECTED FOR PUBLICATION

FIG. 1

BACKGROUND OF THE INVENTION

Field of the Invention

The present invention relates to an analysis system comprising a light source that radiates light and an optical element that reflects or transmits the light irradiated from the light source and a determination method of replacement timing of the optical element of the analysis system.

Description of the Related Art

Conventionally, an analytical device is widely used to carry out an analysis in which the light is radiated to the sample and the light from the sample is measured. In addition, a plurality of analysis devices is connected to a network and an analysis system uses such analysis devices that are controlled with a control terminal via the network.

(1) The analytical devices comprise a light source and a light detector. With respect to the analytical devices, a light is radiated to a sample from the light source, and a light detector detects the light transmitting through the sample or a reflecting light from the sample. And an analysis is carried out based on the detection signal sent from the light detector (e.g., Patent Document 1 below).

With respect to such analytical devices, a lamp used as the light source therefor deteriorates along with that the use time passes and as a result, the light amount of the light detected by the light detector lessens. When the light amount of the light detected by the light detector lessens, such a decrease adversely effects the analysis. Therefore, the light source relative to the analytical device must be periodically replaced with the new light source.

According to the analytical device disclosed in Patent Document 1, the lighting time of the light source is cumulated and when such a lighting time passes over the constant time, the notification for replacement of the light source is controllably carried out.

RELATED PRIOR ART DOCUMENTS

Patent Document

Patent Document 1: JP Patent Published 2001-317997 A1

ASPECTS AND SUMMARY OF THE INVENTION

Objects to be Solved

With respect to the above conventional analytical device, even when the light source is replaced, the light amount of the light detected by the light detector might not meet the predetermined amount. Specifically, the analytical device comprises a variety of optical elements from which the light reflects or through which the light transmits. And while using the analytical device, such an optical element is contaminated with dirt and deteriorates due to ultraviolet light. And when the light from the light source is introduced to the light detector using such a deteriorated optical element, the light amount of the light detected by the light detector lessens even when the appropriate amount of the light is radiated from the light source.

In such a way, with respect to the above conventional analytical device, even when the light source is replaced, the light amount of the light detected by the light detector might not meet the required amount resulting in the failure in which the analytical precision worsens.

The present invention is completed under consideration of the above circumstance, and the purpose of the present invention is to provide an analysis system that is feasible to adequately maintain the light amount of the light detected by the light detector and a determination method of replacement of the optical element of such an analysis system.

Means for Solving the Problem (1) An analysis system according to the aspect of the present invention comprises a light source, a light element, a light detector, and a replacement timing determination unit. The light source radiates the light for carrying out an analysis. The optical element reflects the light radiated from the light source or allows the light to transmit therethrough. The light detector detects the light reflected from the optical element or the light transmitting the optical element. The replacement timing determination unit determines the replacement timing of the optical element based on the light amount of the light detected by the light detector when the light source is replaced With regard to the analysis system, when the optical element deteriorates, the light amount of the light detected by the light detectors lessens. In addition, with regard to the analysis system, the longer the use time of light source is, the lesser the light amount of the light radiated from the light source is due to consumption of the light source. And, as a result, the light amount of the light detected by the light detector lessens. Therefore, when the light source is being continuously used and in addition, the light amount of the light detected by the light detector lessens, both deterioration of the light source and deterioration of the optical element contribute the decrease of the light amount. Accordingly, it is difficult to correctly determine the deterioration of the optical element based on the light amount of the light detected by the light detector under the condition in which the light source is being continuously used.

According to the aspect of the present invention set forth above, with respect to the analytical device, the replacement timing determination unit determines the replacement timing of the optical element based on the light amount of the light detected light detector when the light source is replaced. Therefore, the replacement timing determination unit determines the replacement timing of the optical element based on the light amount of the light detected by the light detector that is not deteriorated. As a result, the replacement timing of the optical element is correctly determined.

And when the optical element is replaced based on that the replacement timing determination unit determines the replacement timing of the optical element, so that the replacement of the optical element is carried out at an adequate timing. As a result, with respect to the analysis system, it is preventable that the further deteriorated optical element is being used. Consequently, the light amount of the light detected by the light detector is maintained at the higher constant level. In such a way, with respect to the analysis system according to the aspect of the present invention, the light amount of the light detected by the light detector is adequately assured.

(2) In addition, the replacement timing determination unit may determine the replacement timing of the optical element at the time when the light amount of the light detected by the light detector, when the light source is replaced, is less than a threshold value.

According to such an aspect, the replacement timing of the light source can be correctly determined with the replacement timing determination unit.

(3) In addition, the analysis system may further comprise a light amount prediction unit. The light amount prediction unit predicts the light amount of the light detected by the light detector when the light source is replaced next time. The replacement timing determination unit may determine the replacement timing of the optical element when the light amount predicted by the light amount prediction unit is less than the threshold value.

According to such an aspect, the replacement timing determination unit determines whether the optical element should be replaced or not on the basis of the replacement timing next time. Specifically, the replacement timing determination unit determines the replacement timing of the optical element in advance.

Therefore, the light amount of the light detected by the light detector is adequately assured.

(4) In addition, the analysis system may further comprise a setting receiving unit. The setting receiving unit receives (accepts) the setting of the threshold value.

According to such an aspect, the threshold value that is the benchmark for determining the replacement timing.

(5) In addition, the analysis system may further comprise a memory storage and an operator receiving unit. The memory storage stores the cumulative time while the light source is being used. The operation receiving unit receives the reset of the cumulative time, while the light source is being used, stored in the memory storage when the light source is replaced. The replacement timing determination unit may determine the replacement timing of the optical element based on the light amount of the light detected by the light detector when the operation receiving unit receives the reset operation.

According to such an aspect, the replacement timing determination unit determines the replacement timing of the optical element when the operation receiving unit receives the reset operation to reset the cumulative time.

Therefore, the replacement timing determination unit determines the replacement timing of the optical element at the adequate timing.

(6) The replacement timing determination method according to the aspect of the present invention is the replacement timing determination method for the optical element with respect to the analysis system comprising the light source that radiates light used for the analysis, the optical element that reflects the light radiated from the light source or through which the light therefrom transmits, and the light detector that detects the light deflected from the optical element or the light that transmits therethrough. The replacement timing determination methods of the optical element comprises a step of determining the replacement timing. The replacement timing of the optical element is determined based on the light amount of the light detected by the light detector upon replacing the light source at the replacement timing determination step.

(7) In addition, the replacement timing determination unit may determine that the optical element should be replaced when the light amount of the light detected by the light detector, when replacing the light source, is less than the threshold value at the replacement timing determination step.

(8) In addition, the replacement timing determination methods of the optical element may further comprise a step of predicting the light amount. When the light source is replaced, the light amount of the light detected by the light detector at the next replacement timing of the light source is predicted at the step of predicting the light amount. The replacement timing determination unit may determine that the time is the replacement timing of the optical element when the light amount predicted at the step of predicting the light amount is less than the threshold value at the step of determining the replacement timing.

Effects of the Present Invention

According to the aspect of the present invention, the replacement timing determination unit determines the replacement timing of the optical element based on the light amount of the light detected by the light detector while the light source is not deteriorating. Therefore, the replacement timing of the optical element is correctly determined. As a result, the light amount of the light detected by the light detector is adequately assured.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
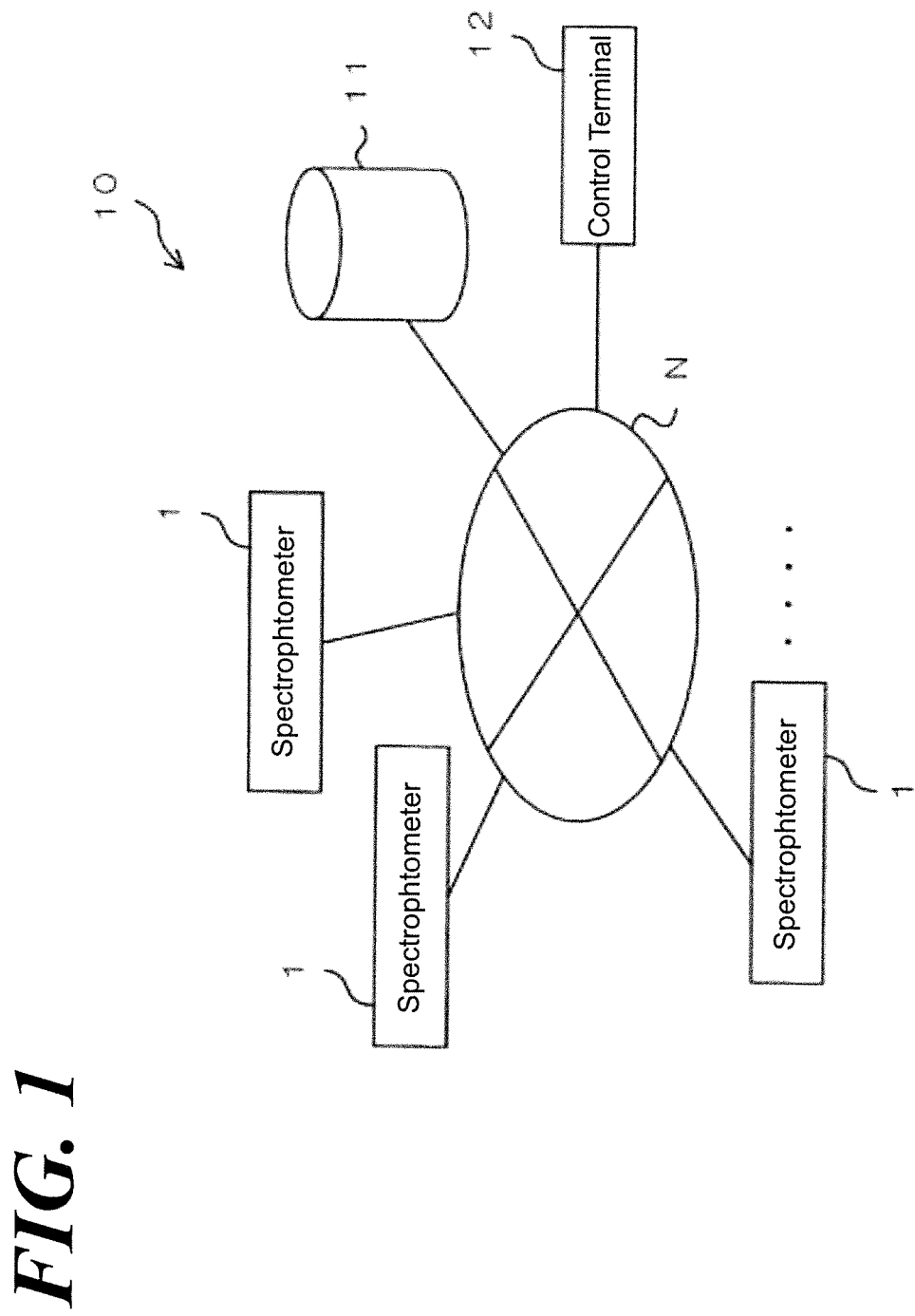
FIG. 1 is a schematic diagram illustrating an example of the structure of an analysis system according to the aspect of the Embodiment 1 of the present invention.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

1. Structure of the Analysis System

FIG. 1 is a schematic diagram illustrating an example of the structure of an analysis system 10 according to the aspect of the Embodiment 1 of the present invention.

The analysis system 10 comprises a plurality of spectrophotometers 1, the memory storage 11, and the control terminal 12. Each spectrophotometer 1 is communicable with the memory storage 11 and the control terminal 12 via the network N.

The analysis system 10 stores the information relative to the light amount of the light from the light source of each spectrophotometer 1 in the memory storage 11 via the network N. The control terminal 12 reads out the information stored in the memory storage 11 via the network N and then, determines the replacement timing of the optical element of each spectrophotometer 1 based on the read-out information.

Figure 2:
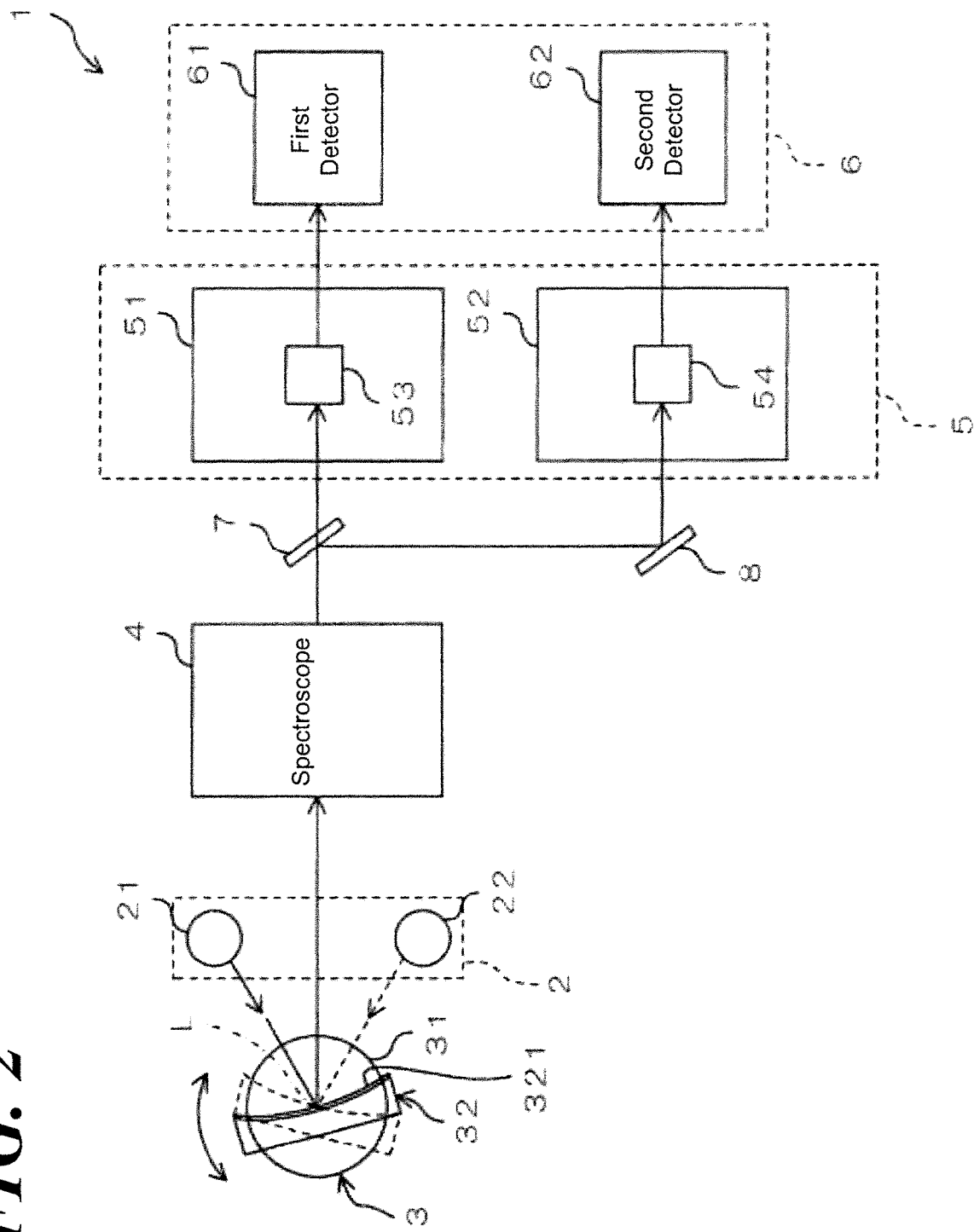
FIG. 2 is a schematic view illustrating an example of the structure of a spectrophotometer in FIG. 1.

FIG. 2 is a schematic diagram illustrating an example of the structure of the spectrophotometer 1. The spectrophotometer 1 is a spectrophotometer that uses the light belonging to the UV region, the visible light region and the near infrared light region (mensurative light). The spectrophotometer 1 comprises the light source 2, the light source switching unit 3, the spectroscope 4, the sample loading unit 5 and the light detector 6.

The light source 2 radiates the mensurative light and comprise the first light source 21 and the second light source 22.

The first light source 21 comprises a deuterium lamp (D2 lamp). The second light source 22 comprises a tungsten lamp (WI lamp). The first light source 21 and the second light source 22 are in-place apart from each other with some distance.

The light source switching unit 3 is in-place apart from the light source 2 with some distance. The light source switching unit 3 selectively switches the light from between the first light source 21 and the second light source 22, so that the selected light is incident to the first light detector 61 and the second light detector 62. The light source switching unit 3 comprises the rotation unit 31 and the switching mirror 32.

The rotation unit 31 is a circular disc. The rotation unit 31 is rotatable around the axis-line L as the rotation center. The rotation unit 31 rotates with a predetermined rotation angle by being provided with a driving force.

The switching mirror 32 is installed on the rotation unit 31. The switching mirror 32 is a concave mirror of which reflecting surface 321 is formed as a concave. The reflecting surface 321 of the switching mirror 32 faces the light source 2.

The spectroscope 4 is in-place in the opposite side of the light source switching unit 3 relative to the light source 2. The spectroscope 4 disperses the light from the light source 2. Despite not showing in FIG., the spectroscope 4 comprises a filter that cuts unwanted high-dimensional lights and the grating that takes out the light having a specific wavelength, a mirror that reflects the lights and so forth, and further a split, through which the light passes, is installed thereto.

The sample loading unit 5 is the unit to load the sample. According to the aspect of the present Embodiment, two samples (one for the mensurative sample and another one for the reference sample) for measurement and are loaded to the sample loading unit 5. The sample loading unit 5 comprises the first sample chamber 51, the second sample chamber 52 and the sample cells 53, 54.

The first sample chamber 51 and the second sample chamber 52 are respectively in-place apart from each spectroscope 4 with some distance. The sample cell 53 is in-place inside the first sample chamber 51 and the sample cell 54 is in-place inside the second sample chamber 52. The sample cell 53 holds the mensurative sample and the sample cell 54 holds the reference sample (not shown in FIG.). Despite not showing in FIG., the first sample chamber 51 and the second sample chamber 52 comprise respectively a split through which the light passes.

A half-mirror 7 is in-place between the spectroscope 4 and the first sample chamber 51. The half-mirror 7 enables passing part of the incident light and reflecting the rest part of the incident light. The mirror 8 is in-place apart from the half-mirror 7 with some distance. The mirror 8 faces the second sample chamber 52.

The light detector 6 is the detector to detect lights that are radiated to the sample in sample loading unit 5. According to the aspect of the present Embodiment, the light detector 6 comprises the first detector 61 and the second detector 62.

The first detector 61 is in-place apart from the first sample chamber 51 with some distance. The second detector 62 is in-place apart from the second sample chamber 52 with some distance. The first detector 61 and the second detector 62 respectively detects the incident light and outputs the signal corresponding to the light intensity.

The spectrophotometer 1 is a so-called a double-beam spectrophotometer and the light radiated from the light source 2 is irradiated respectively to the mensurative sample and the reference sample in the sample loading unit 5. And the light from either one of the first light source 21 or the second light source 22 selected from the light source 2 is incident to the spectroscope 4.

Specifically, when the analysis is carried out using the spectrophotometer 1, an angle of the reflecting surface 321 of the switching mirror 32 is adjusted by rotating the rotation unit 31. And the light radiated from either the first light source 21 or the second light source 22 is selectively reflected so as to be incident to the spectroscope 4.

And the grating inside the spectroscope 4 disperses the incident light to the spectroscope 4 to lights having each specific wavelength. And then, only the dispersed light having the specific wavelength is radiated from the spectroscope 4. In addition, the light repeatedly reflects multiple times at a plurality of mirrors in the spectroscope 4 and is radiated to outside of the spectroscope 4. A part of the lights radiated to outside the spectroscope 4 is incident to the first sample chamber 51 following transmitting through the half-mirror 7 and then, radiates the sample cell 53 (i.e., the mensurative sample). In addition, the lights (rest of the light) radiated to outside the spectroscope 4 and reflected from the mirror 8 is incident to the second sample chamber 52 following reflecting from the half-mirror 7 and then, radiates the sample cell 54 (sample for reference).

And the first detector 61 detects the light transmitting through the sample cell 53 (mensurative sample) or the light (reflecting light) reflected therefrom. In addition, the second detector 62 detects the light transmitting through the sample cell 54 (sample for the reference) or the light reflected therefrom.

Each of the first detector 61 and the second detector 62 outputs the detection signal in accordance with the detected light thereby. The spectrophotometer 1 generates the spectrum related to the mensurative sample based on the detection signals of the first detector 61 and the second detector 62 following eliminating an effect due to a fluctuation. And the analysis of the mensurative sample is performed based on the generated spectrum.

With respect to the spectrophotometer 1, when the above analysis operation is repeated, the optical element is contaminated with dirt and deteriorates due to ultraviolet light. And when the light from the light source 2 is introduced to the light detector 6 using such a deteriorated optical element, the light amount of the light detected by the light detector 6 lessens. The analysis system 10 comprises the following components to resolve such a malfunction and in addition, the following control operation is carried out.

In addition, with respect to the spectrophotometer 1, the optical element is a member in-place in the light path, through which the light transmits and by which the light is reflected. For example, the optical element comprises the switching mirror 32 of the light source switching circuit 3, the mirror and the grating inside the spectroscope 4, the half-mirror 7 and the mirror 8.

2. Electrical Configuration of the Analysis System

Figure 3:
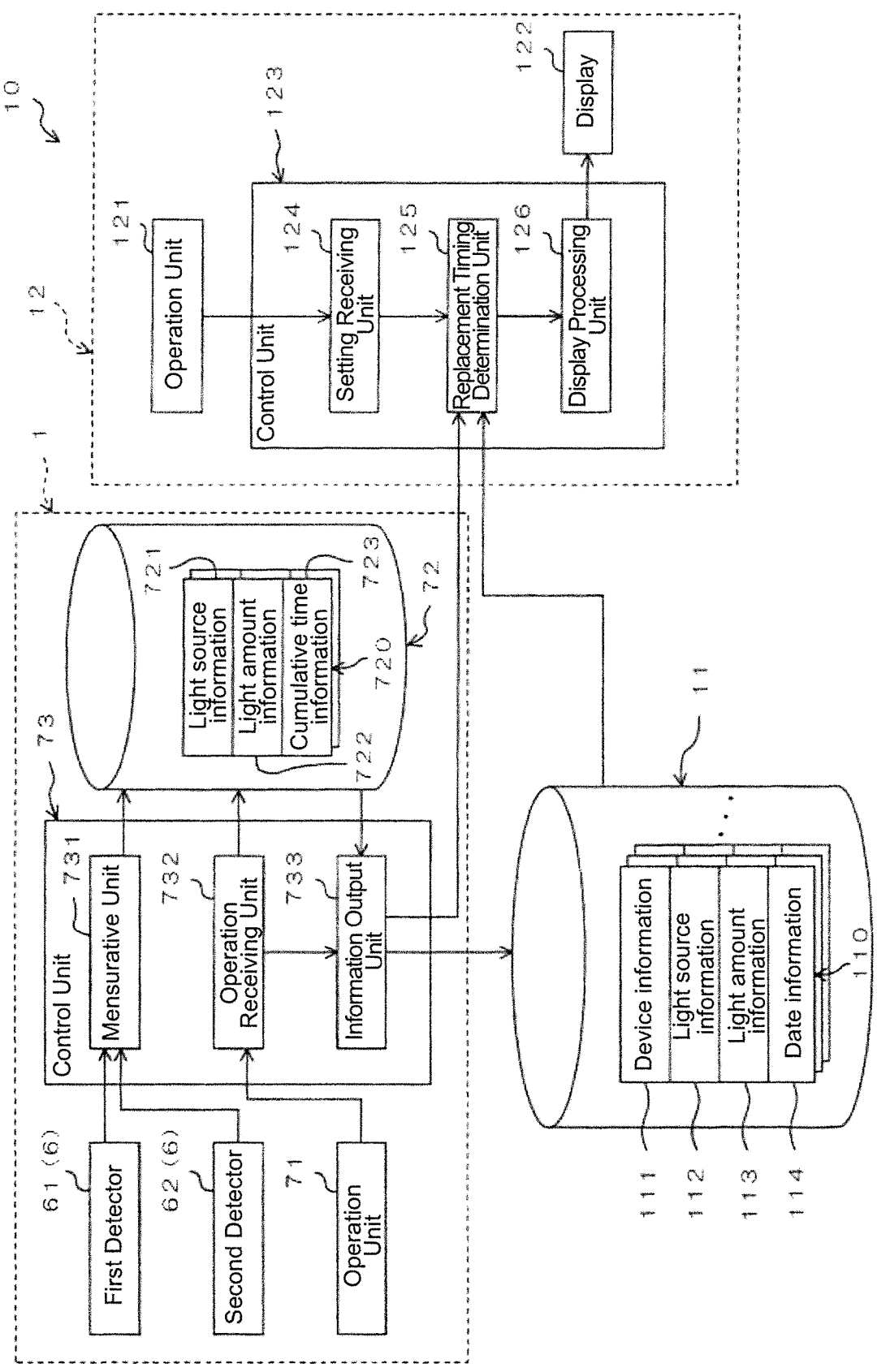
FIG. 3 is a block diagram illustrating an electrical configuration of the analysis system in FIG. 1.

FIG. 3 is a block diagram illustrating the electrical configuration of the analysis system 10. In addition, referring to FIG. 3, for convenience sake, only one spectrophotometer 1 is illustrated, but also other spectrophotometers 1 electrically connects with the memory storage 11 and the control terminal 12 as well as the spectrophotometer 1 illustrated in FIG. 3.

(1) Spectrophotometer

The spectrophotometer 1 further comprises an operation unit 71, the memory storage 72, the control unit 73 and so forth as an electrical component thereof in addition to the first detector 61 and the second detector 62.

The operation unit 71 comprises, for example, a keyboard and a mouse.

The memory storage 72 comprises such as ROM (read only memory), RAM (random access memory) and a hard-disk drive. The memory storage 72 stores the operation information 720. According to the aspect of the present Embodiment, the memory storage 72 stores two kinds of the operation information 720. Each operation information 720 is related to the operation of each light source of light source 2. Specifically, the one of the operation information 720 is the information related to the operation of the first light source 21 and the other one of the operation information 720 is the information related to the operation of the second light source 22. The operation information 720 includes the light source information 721, the light amount information 722 and the cumulative time information 723.

The light source information 721 denotes the kind of the light source 2 (the first light source 21 or the second light source 22).

The light amount information 722 is the information related to the light amount of the light detected by the light detector 6 (the first detector 61 and the second detector 62).

The cumulative time information 723 is the information related to the cumulative time while the light source (the first light source 21 or the second light source 22) of the light source 2 is being operated.

The control unit 73 comprises e.g., a CPU (central processing unit). The control element 73 electrically connects with such as the first detector 61, the second detector 62, the operation unit 71 and the memory storage 72. When the CPU executes a program, the control unit 73 is operative as a mensurative processing unit 731, an operation receiving unit 732, and an information output unit 733 and so forth.

The mensurative processing unit 731 measures the operation time of the light source of the light source 2 and the light amount thereof based on the detection signal from the first detector 61 and the detection signal of the second detector 62 and then, stores the measurement information thereof in the memory storage 72.

In addition, the operation receiving unit 732 receives the input operation at the operation unit 71.

The information output unit 733 executes a processing to output the information stored in the memory storage 72 to the memory device 11. In addition, the information output unit 733 executes a processing to output the signal to the control terminal 12 in accordance with that the operation receiving unit 732 receives the input operation.

(2) Memory Device

The memory device 11 is the memory device (storage) is communicable with each spectrophotometer 1 and the control terminal 12 via the network N. The memory device 11 comprises such as e.g., a hard disk drive. The memory device 11 stores a plurality of control information 110. Each control information 110 is the information related to the state of the optical element relative to each spectrophotometer 1. The control information 110 includes the device information 111, the light source information 112, the light amount information 113 and the date information 114.

The control information 111 is the information to identify the one spectrophotometer 1 from a plurality of the spectrophotometers 1. Specifically, the device information 111 is an ID (identification data) denoting the specific spectrophotometer 1. The light source information 112 denotes the kind of the light source of the light source 2 (the first light source 21 or the second light source 22) of the spectrophotometer 1. The light amount information 113 is the information related to the light amount of the light detected by the light detector 6 (the first detector 61 and the second detector 62) of the spectrophotometer 1. The date information 114 is the information related to the date and time when the light source of the light source 2 of the spectrophotometer 1 is replaced.

(3) Controller Terminal

The control terminal 12 is the terminal to control each spectrophotometer 1 via the network N, and comprises e.g., a variety of devices and units such as a personal computer. The control terminal 12 comprises the operation unit 121, the display 122 and control circuit 123 and so forth. The operation unit 121 comprises, for example, a keyboard and a mouse. The display 122 comprises e.g., a liquid crystal display.

The control unit 123 comprises e.g., a CPU (central processing unit). The control unit 123 electrically connects with the operation unit 121 and the display 122 and so forth. In addition, the information from each spectrophotometer 1 and the memory device 11 are input into the control unit 123 via the network N. When the CPU executes a program, the control unit 123 is operative as the setting receiving unit 124, the replacement timing determination unit 125, and the display processing unit 126 and so forth.

The setting receiving unit 124 receives an input operation (setting) at the operation unit 121 by the user.

The replacement timing determination unit 125 determines the replacement timing of the optical element of each spectrophotometer 1 based on the information stored in the memory device 11.

The display processing unit 126 executes the processing to display the predetermined display content on the display 122 based on that the replacement timing determination unit 125 determines the replacement timing of the optical element.

3. Operation Along with the Replacement Timing Determination of the Optical Element When the spectrophotometer 1 performs an analytical operation, the mensurative processing unit 731 stores the operation information 720 in the memory storage 72 based on the detection signal from the first detector 61 and the detection signal of the second detector 62.

For example, with respect to the spectrophotometer 1, when the light from the first light source 21 is incident to the light detector 6, the mensurative processing unit 731 classifies the information belonging to the first light source 21 as the light source information 721, the information belonging to the light amount detected by the light detector 6 when the first light source 21 first radiates the light, while no sample is being set, as the light amount information 722 and the time, while the first light source 21 is cumulatively running, as the cumulative time information 723, and then, stores such information and time in the memory storage 72 as the operation information 720 while relating such information and time to each other.

In addition, for example, with respect to the spectrophotometer 1, when the light from the second light source 22 is incident to the light detector 6, the mensurative processing unit 731 classifies the information belonging to the second light source 22 as the light source information 721, the information belonging to the light amount detected by the light detector 6 when the second light source 22 first radiates the light, while no sample is being set, as the light amount information 722 and the time, while the second light source 22 is cumulatively running, as the cumulative time information 723, and then, stores such information and time in the memory storage 72 as the operation information 720 while relating such information and time to each other.

According to the aspect of the present Embodiment, first, the light source (the first light source 21 or the second light source 22) radiates the light to each cell 53, 54 with no sample. And the information relative to the light amount detected by the light detector 6 is obtained when the light source radiates first time. Then after, the analytical operation starts following loading the sample in each cell 53, 54. Then, the information relative to the operation time of the light source is obtained. The memory storage 72 of the spectrophotometer 1 stores the operation information 720 corresponding to the first light source 21 and the operation information 720 corresponding to the second light source 22. In addition, while each light source is running, the cumulative time information 723 of each operation information 720 is updated as needed by the mensurative processing unit 731. Such operation information 720 are applied, for example, when the user is about to check the operational circumstance of the spectrophotometer 1.

With respect to the spectrophotometer 1, when the cumulative running time of the light source is over the constant time, the user replaces such a light source to the new light source. In addition, at that time, the user runs the operation unit 71 to input a directive to reset (carry out a reset-operation) the operation information 720 stored in the memory storage 72. The operation receiving unit 732 accepts the reset operation at the operation unit 71 by the user and in addition, resets the cumulative time information 723 corresponding to the operation information 720. In addition, the mensurative processing unit 731 rewrite the light amount of the light detected by the light detector 6 as the light amount information 722 when the light source is replaced to the new light source (right after replacement) and also, rewrites the time while the new light source is cumulatively running as the cumulative time information 723.

For example, when the user runs the operation unit 71 to input a directive to reset (carry out a reset-operation) the operation information 720 relative to the first light source 21 when the first light source 21 of the spectrophotometer 1 is replaced to the new light source. The operation receiving unit 732 receives the reset operation from the user and in addition, resets the cumulative time information 723 among the operation information 720 relative to the first light source 21. In addition, the mensurative processing unit 731 newly rewrites the information of the light amount of the light, which is radiated from the first light source 21 right after the replacement in the circumstance in which no sample is loaded in each sample cell 53, 54, detected by the light detector 6, right after replacement of the light source, as the light amount information 722. In such a way, once the reset operation by the user is accepted, the measurement is automatically carried out under the circumstance in which no sample is loaded in the sample cell 53, 54.

At this time, the information output unit 733 outputs the electric signal to the control terminal 12 (to start the determination processing) in accordance with that the operation receiving unit 732 accepts the reset operation, and in addition, outputs the operation information 720 in the memory storage 72 to the memory device 11.

The memory device 11 stores the information specifying the spectrophotometer 1 subjected to the reset operation as the device information 111, the information of the replaced light source in such a spectrophotometer 1 as the light source information 112, the information of the light amount of the light detected by the light detector 6 right after replacement of the light source as the light source information 113, and the information of the date, when the light source is replaced, as the date information 114, and further, stores such information as the control information 110 while relating such information to each other. Each of the light source information 112 information 110 of the control information 110 and the light amount information 113 thereof is respectively correspond to each of the light source information 721 and light amount information 722 in the memory storage 72.

In such a way, the memory device 11 stores a variety of information as the control information 110 relative to the light amount of the light detected by the light detector 6 right after replacement of the light source when the light source of each spectrophotometer 1 is replaced. The memory device 11 stores the control information 110 every time when the light source of the spectrophotometer 1 is replaced, so that the memory device 11 stores a plurality of control information 110.

In addition, the control terminal 12 determines whether the optical element of the spectrophotometer 1 should be replaced or not in accordance with the signal input from the spectrophotometer 1.

Figure 4:
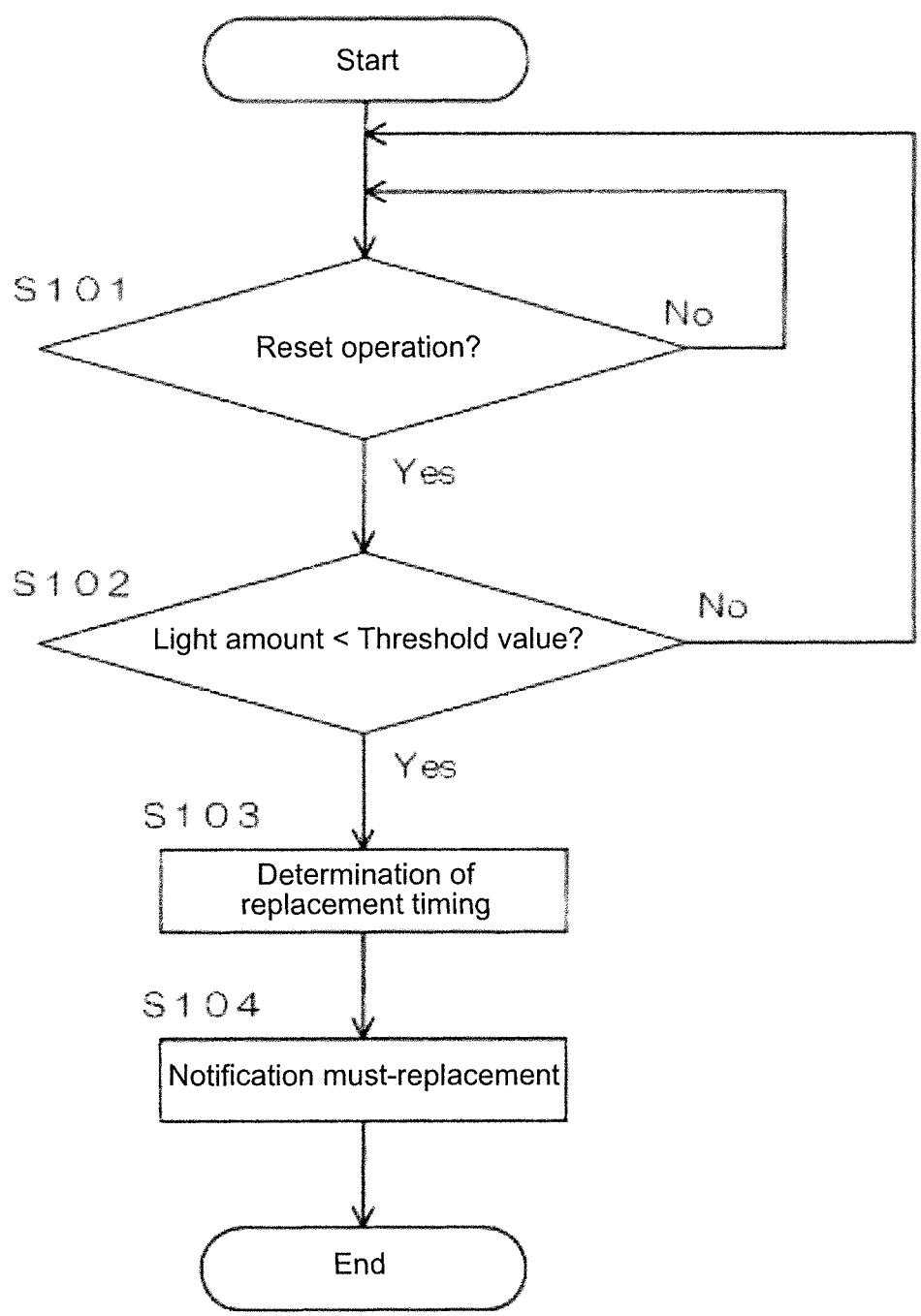
FIG. 4 is a flow-chart illustrating an example of the control operations of the control terminal in FIG. 1.

FIG. 4 is the flow-chart illustrating an Embodiment relative to control operations of the control terminal 12.

The replacement timing determination unit 125 reads out the control information 110 stored in the memory device 11 in accordance with the signal input from the information output unit 733 of the spectrophotometer 1. Specifically, the replacement timing determination unit 125 reads out the control information 110 stored in the memory device 11 in accordance with that the spectrophotometer 1 receives the reset operation (Yes at the step S101). Specifically, the control terminal 12 reads out the control information 110 relative to the light source on which the reset operation is carried out.

At this time, the replacement timing determination unit 125 of the control terminal 12 may read out one of the control information 110 from a plurality of control information 110 using the date information 114 as an index. For example, the replacement timing determination unit 125 may read out the control information 110 in which the date information 114 is updated as the newest information.

And the replacement timing determination unit 125 determines whether the read-out value of the light amount information 113 of the control information 110 is less than the threshold value or not. When the value of the light amount information 113, i.e., the light amount of the light right after replacement, is less than the threshold value (Yes at the step S102, i.e., the replacement timing determination step), the replacement timing determination unit 125 determines that such a spectrophotometer 1 (the spectrophotometer 1 that the device information 111 identifies) is in the replacement timing of the optical element thereof (the step S103). In addition, the display processing unit 126 displays that the optical element of the spectrophotometer 1 is in the replacement timing on the display 122 and reminds the user that the optical element should be replaced (the step S104). And the controller decides the replacement of the optical element of the spectrophotometer 1 based on the reminder displayed on the display 122.

In such a way, the controller checks the replacement timing of the optical element of the spectrophotometer 1 and goes to the site (or sends an operator to the site) to replace the optical element of the spectrophotometer 1 based on the check result.

In addition, the controller operates the operation unit 121 (carries out the setting operation) at the control terminal 12 to set up the threshold value being applied to the replacement timing determination relative to the optical element. When the controller sets up the threshold value by operating the operation unit 121, the setting receiving unit 124 accepts such a setting. Then, the replacement timing determination unit 125 carries out the determination based on the threshold value that the setting receiving unit 124 accepts the step S102.

In addition, the control unit 123 of the control terminal 12 may decide an adequate threshold value based on a plurality of control information 110 stored in the memory device 11. For example, the control unit 123 obtains an average value from the light source information 112 relative to a plurality of optical element information 110 and may decide the adequate threshold value based on such an average value.

Then, the replacement timing determination unit 125 may carry out the determination based on the threshold value decided at the step S102.

Figure 5:
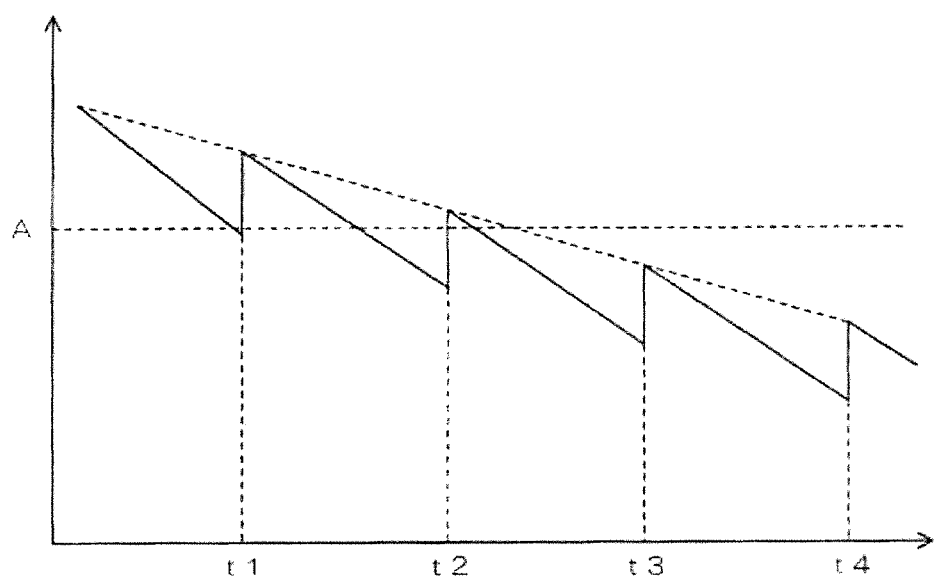
FIG. 5 is a graph illustrating the time-course variation of the light amount of the light detected by the light detector of the spectrophotometer in FIG. 1.

FIG. 5 is a graph illustrating the time-course variation of the light amount of the light detected by the light detector 6 of the spectrophotometer 1. Referring to FIG. 5, the horizontal axis denotes the operation time (running time) of the spectrophotometer 1 and the vertical axis denotes the light amount of the light detected by the light detector 6. With respect to the spectrophotometer 1 corresponding to FIG. 5, the light source is replaced at the times t1-t4.

Referring to FIG. 5, as indicated by the solid line, the light amount of the light detected by the light detector 6 gradually decreases over the operation time. And the light amount of the light detected by the light detector 6 sharply increase (rebounds) at the timing right after each time t1-t4. On the other hand, as indicated by the broken line, the rebound light amount of the light detected by the light detector 6 decreases over time (the later the time is, the lesser the amount is) even right after the light source is replaced. The reason is that, with respect to the spectrophotometer 1, the optical element is contaminated with dirt and deteriorates due to ultraviolet light.

According to the analysis system 10, the light amount of the light detected by the light detector 6 is compared to the threshold value at the time right after the light source is replaced (each timing t1-t4), so that the deterioration of the optical element is correctly evaluated. Referring to FIG. 5, according to the aspect of the present Embodiment, the light amount of the light detected by the light detector 6 is less than the threshold value A at the timing t3. Therefore, the control terminal 12 notifies on the display 122 that the optical element of the spectrophotometer 1 must be replaced at the timing t3 or at the timing right after the timing t3.

4. Action and Effect (1) According to the aspect of the present Embodiment, the analysis system 10 comprises a plurality of spectrophotometers 1, the memory storage 11, and the control terminal 12. The spectrophotometer 1 further comprises the light source 2, the light detector 6, and the optical element that introduces the light from the light source 2 to the light detector 6. The control terminal 12 further comprises the control unit 123. The control unit 123 further comprises the setting receiving unit 124.

The memory device 11 stores the information (control information 110) relative to the light amount of the light detected by the light detector 6 right after replacement of the light source when the light source of each spectrophotometer 1 is replaced.

The control terminal 12 reads out the control information 110 in the memory device 11 and determines the replacement timing (step S103 in FIG. 4) based on the light amount information 113 of the read-out control information 110.

Specifically, the replacement timing determination unit 125 of the control terminal 12 determines the replacement timing of the optical element of the spectrophotometer 1 based on the light amount of the light detected by the light detector 6 under the condition in which that the light source of the spectrophotometer 1 is not deteriorating.

Therefore, the replacement timing of the optical element of the spectrophotometer 1 is correctly determined.

And when it is the replacement timing of the optical element of the spectrophotometer 1, the display 122 notifies such a timing.

Therefore, it is feasible that the light amount of the light detected by the light detector 6 of the spectrophotometer 1 is adequately assured.

(2) And, according to the aspect of the present Embodiment, the replacement timing determination unit 125 of the control terminal 12 reads out the control information 110 in the memory device 11 and determines whether the read-out value of the light amount information 113 of the control information 110 is less than the threshold value or not. When the value of the light amount information 113, i.e., the light amount of the light right after replacement, is less than the threshold value (Yes at the step S102 in FIG. 4, i.e., the replacement timing determination step), the replacement timing determination unit 125 determines that such a spectrophotometer 1 (the spectrophotometer 1 that the device information 111 identifies) is in the replacement timing of the optical element thereof (the step S103 in FIG. 4).

Therefore, the replacement timing of the light source of the spectrophotometer 1 can be correctly determined with the replacement timing determination unit 125 of the control terminal 12.

(3) In addition, referring to FIG. 3 according to the aspect of the present Embodiment, the control unit 123 of the control terminal 12 further comprises the setting receiving unit 124. When the controller sets up the threshold value by operating the operation unit 121, the setting receiving unit 124 accepts such a setting. Then, the replacement timing determination unit 125 carries out the determination based on the threshold value that the setting receiving unit 124 accepts at the step S102 in FIG. 4.

Accordingly, the threshold value that is the benchmark for determining the replacement timing using the control terminal 12 is adequately set up.

(4) In addition, referring to FIG. 3, according to the aspect of the present Embodiment, the spectrophotometer 1 further comprises the memory storage 72 and the operation unit 71. The control unit 73 further comprises the operation receiving unit 732. The memory storage 72 stores the operation information 720. The cumulative time information 723 of the operation information 720 is the information related to the cumulative time while the light source (the first light source 21 or the second light source 22) of the light source 2 is being operated.

With respect to the spectrophotometer 1, when the light source is replaced, and the user runs the operation unit 71 to input a directive to reset the operation information 720, the operation receiving unit 732 accepts the reset operation therefor. The memory device 11 stores the information relative to the light amount of the light detected by the light detector 6 when the reset operation with respect to the spectrophotometer 1 is accepted thereby. And with respect to the control terminal 12, the replacement timing determination unit 125 reads out the control information 110 in the memory device 11 and then, determines the replacement timing of the optical element based on the light amount information 113 of the read-out control information 110.

Therefore, the replacement timing determination unit 125 of the control terminal 12 determines the replacement timing of the optical element at the adequate timing.

5. Embodiment 2

Figure 6:
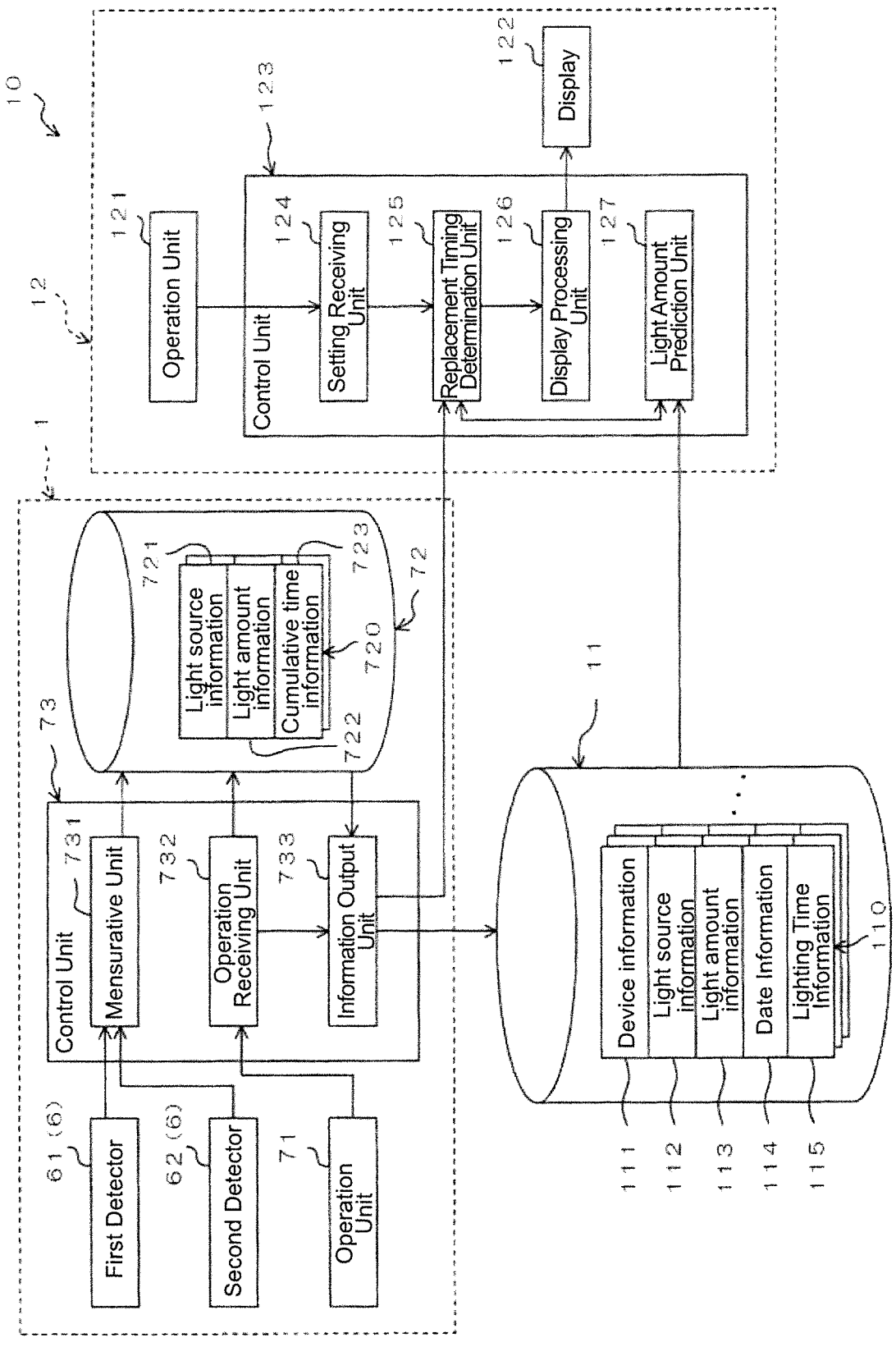
FIG. 6 is a block diagram illustrating an electrical configuration of the analysis system according to the aspect of the Embodiment 2 of the present invention.

Hereafter, the inventor sets forth the analysis system 10 according to the aspect of the Embodiment 2 of the present invention referring to FIG. 6. In addition, the same unit as illustrated according to the aspect of the Embodiment 1 is not set forth while providing the identical reference sign.

FIG. 6 is a block diagram illustrating an electrical configuration of the analysis system 10 according to the aspect of the Embodiment 2 of the present invention.

According to the aspect of the Embodiment 1, the replacement timing determination unit 125 of the control terminal 12 reads out the control information 110 in the memory device 11 and then, determines the replacement timing of the optical element based on the light amount information 113 of the read-out control information 110.

Whereas, according to the aspect of the Embodiment 2, the replacement timing determination unit 125 of the control terminal 12 determines the replacement timing of the optical element based on the light amount predicted by the light amount prediction unit 127.

Specifically, according to the aspect of the Embodiment 2, the control information 110 in the memory device 11 comprises a lighting time information 115.

The lighting time information 115 is the information relative to the total lighting time of the replaced light source of the spectrophotometer 1 and corresponds to the cumulative time information 723 of the operation information 720 stored in the memory storage 72.

In addition, the control unit 123 of the control terminal 12 further comprises a light amount prediction unit 127.

According to the aspect of the Embodiment 2, at the step S102 in FIG. 4, the light amount prediction unit 127 predicts the light amount of the light detected by the light detector 6 at the next replacement timing of the following light source for the spectrophotometer 1 and then, the replacement timing determination unit 125 determines the replacement timing of the light source based on the prediction result thereof.

Specifically, with respect to the analysis system 10, when receiving the reset operation relative to the spectrophotometer 1 as set forth above, the light amount prediction unit 127 reads out the control information 110 stored in the memory device 11.

And the light amount prediction unit 127 reads the transition of the detection light amount of the light detected by the light detector 6 on the past replacement time of the light source so far, and then, predicts the detection light amount of the light detected by the light detector 6 at the next replacement time of the light source based on such an information (the light amount prediction step). The replacement timing determination unit 125 determines whether the light amount predicted by the light amount prediction unit 127 is less than the threshold value or not, and determines the time is the replacement timing of the light source of the spectrophotometer 1 when the light amount predicted by the light amount prediction unit 127 is less than the threshold value (the step S103), For example, the light amount prediction unit 127 calculates the tilt denoting the decrease of the light amount of the light detected by the light detector 6 of the spectrophotometer 1 as indicated by the broken line in FIG. 5 based on the control information 110. And the light amount prediction unit 127 predicts the detection light amount of the light detected by the light detector 6 at the next replacement timing of the light source of the spectrophotometer 1 based on such a tilt. For example, when the reset operation is accepted at the time t2 in FIG. 5 (when the light source is replaced), the light amount prediction unit 127 predicts the light amount at the time t3 that is the next replacement timing using the tilt indicated by the broken line. And the replacement timing determination unit 125 determines whether the predicted light amount is less than the threshold value A or not. According to the aspect of the Embodiment 2, the light amount at the time t3 when the light amount prediction unit 127 predicts is the less than the threshold value A, so that the replacement timing determination unit 125 determines that the optical element of the spectrophotometer 1 is in the replacement timing.

In such a way, according to the aspect of the present Embodiment 2 referring to FIG. 6, the control unit 123 of the control terminal 12 comprises the light amount prediction unit 127. The light amount prediction unit 127 predicts the light amount of the light detected by the light detector 6 at the next replacement timing of the light source when the light source of the spectrophotometer 1 is replaced. The replacement timing determination unit 125 determines that the optical element of the spectrophotometer 1 is in the replacement timing when the light amount being predicted by the light amount prediction unit 127 is less than the threshold value.

Therefore, the replacement timing determination unit 125 of the control terminal 12 determines whether the optical element of the spectrophotometer 1 should be replaced or not on the basis of the replacement timing next time. Specifically, the replacement timing determination unit 125 determines the replacement timing of the optical element of the spectrophotometer 1 in advance.

As a result, the light amount of the light detected by the light detector 6 of the spectrophotometer 1 is adequately assured.

6. Alternative Embodiment

According to the aspect of the Embodiment set forth above, the control unit 123 of the control terminal 12 that is communicable with the spectrophotometer 1 via the network N determines the replacement timing of the optical element of the spectrophotometer 1. Whereas, the control unit 73 of the spectrophotometer 1 may determine the replacement timing of the optical element of the spectrophotometer 1. Specifically, the control unit 73 of the spectrophotometer 1 is operative as well as the control unit 123 and also, the spectrophotometer 1 may comprise the display 122. And the replacement timing of the optical element is determined solely by the spectrophotometer 1 per se without involvement of the control terminal 12. In addition, even without connecting to the network. i.e., in so-called a closed environment, the PC (personal computer) for controlling that is electrically connected to the spectrophotometer 1 can be separately equipped thereto. In such a case, the notification relative to the replacement of the optical element can be displayed on the PC screen for control software for controlling without including the display in the spectrophotometer 1.

In addition, according to the aspect of the present Embodiment set forth above, the spectrophotometer 1 comprises two light sources and in addition, such a spectrophotometer 1 is in the class of the double beam system having two detectors. Whereas, the spectrophotometer 1 may comprise just one light source and in addition, such a spectrophotometer 1 may be in the class of the so-called single beam system having one detector. In addition, the spectrophotometer 1 may be in the class of the double beam system having just one detector.

In addition, according to the aspect of the Embodiment set forth above, the light amount of the light detected by the light detector 6 is automatically measured when the reset operation from the user is accepted. Whereas, a sensor that detects the replacement of the light source is separately equipped and the light amount of the light detected by the light detector 6 is automatically measured based on the detection result using the sensor.

REFERENCE OF SIGNS

1 Spectrophotometer
2 Light source
3 Light source switching unit
4 Spectroscope
6 Light detector
7 Half mirror
8 Mirror
21 First light source
22 Second light source
32 Switching mirror
61 First detector
62 Second detector
72 Memory storage
73 Control unit
123 Control unit
124 Setting receiving unit
125 Replacement timing determination unit
127 Light amount prediction unit
723 Cumulative time information
732 Operation receiving unit It will be further understood by those of skill in the art that the apparatus and devices and the elements herein, without limitation, and including the sub components such as operational structures, circuits, communication or data pathways, and related elements, control circuits/elements and detection circuits/elements of all kinds, display circuits and display systems and elements, any necessary driving elements, inputs, sensors, detectors, memory elements, processors and any combinations of these structures etc. as will be understood by those of skill in the art as also being identified as or capable of operating the systems and devices and sub-components noted herein and structures that accomplish the functions without restrictive language or label requirements since those of skill in the art are well versed in related analysis systems and optical element replacement timing and determination methods including any computer and operational controls and technologies of such spectrophotometer devices and all their sub components, including various circuits, elements and combinations of circuits, elements without departing from the scope and spirit of the present invention.

Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Those of skill would further appreciate that the various illustrative logical blocks, modules, circuits, and algorithm steps described in connection with the embodiments disclosed herein may be implemented as electronic hardware, computer software running on a specific purpose machine that is programmed to carry out the operations described in this application, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments.

The various illustrative logical blocks, modules, and circuits described in connection with the embodiments disclosed herein, may be implemented or performed with a general or specific purpose processor, or with hardware that carries out these functions, e.g., a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor can be part of a computer system that also has an internal bus connecting to cards or other hardware, running based on a system BIOS or equivalent that contains startup and boot software, system memory which provides temporary storage for an operating system, drivers for the hardware and for application programs, disk interface which provides an interface between internal storage device(s) and the other hardware, an external peripheral controller which interfaces to external devices such as a backup storage device, and a network that connects to a hard wired network cable such as Ethernet or may be a wireless connection such as a RF link running under a wireless protocol such as 802.11. Likewise, an external bus may be any of but not limited to hard wired external busses such as IEEE-1394 or USB. A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

The steps of a method or algorithm described in connection with the embodiments disclosed herein may be embodied directly in hardware, in a software module executed by a processor, using cloud computing, or in combinations. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of tangible storage medium that stores tangible, non-transitory computer based instructions. An exemplary storage medium is coupled to the processor such that the processor can read information from, and write information to, the storage medium. In the alternative, the storage medium may be integral to the processor. The processor and the storage medium may reside in reconfigurable logic of any type.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer.

The memory storage can also be rotating magnetic hard disk drives, optical disk drives, or flash memory based storage drives or other such solid state, magnetic, or optical storage devices. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-Ray® disc where disks usually reproduce data magnetically, while discs reproduce data optically with lasers. Combinations of the above should also be included within the scope of computer-readable media. The computer readable media can be an article comprising a machine-readable non-transitory tangible medium embodying information indicative of instructions that when performed by one or more machines result in computer implemented operations comprising the actions described throughout this specification.

Operations as described herein can be carried out on or over a web site. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

The computers described herein may be any kind of computer, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, the inventors intend that only those claims which use the words "means for" are intended to be interpreted under 35 USC 112 only when the word 'means' and 'for' are used together, next to each other in the form of "means for", and not otherwise. Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. An analysis system, comprising:
a light source that radiates light for an analysis;
an optical element that is operative for at least one of reflecting said light radiated from said light source and allowing said light to transmit therethrough;
a light detector that detects at least one said light selected from a group consisting of said light reflected from said optical element and said light transmitting through said optical element;
a replacement timing determination unit that determines a replacement timing of said optical element based on a light amount of said light detected by said light detector when replacing said light source; and
a light amount prediction unit that predicts said light amount of said light detected by said light detector when said light source is replaced next time;
wherein said replacement timing determination unit determines that said optical element is said replacement timing thereof when said light amount that said light amount prediction unit predicts meets less than the threshold value.

2. An analysis system, comprising:
a light source that radiates light for an analysis;
an optical element that is operative for at least one of reflecting said light radiated from said light source and allowing said light to transmit therethrough;
a light detector that detects at least one said light selected from a group consisting of said light reflected from said optical element and said light transmitting through said optical element;
a replacement timing determination unit that determines a replacement timing of said optical element based on a light amount of said light detected by said light detector when replacing said light source;
a memory storage that stores a cumulative time while said light source is being used; and
an operation receiving unit that accepts a reset operation of a cumulative time, while said light source is being used, that said memory storage stores when replacing said light source;
wherein said replacement timing determination unit determines that said optical element is in said replacement timing thereof based on said light amount of said light detected by said light detector when said operation receiving unit accepts said reset operation.

3. A replacement timing determination method, of an optical element for an analysis system that comprises:
a light source that radiates light for an analysis;
an optical element that is operative for at least one of reflecting said light radiated from said light source and allowing said light to transmit therethrough;
a light detector that detects at least one said light selected from a group consisting of a reflected light from said optical element and a transmitting light through said optical element,
an operation unit; and
an operation receiving unit, comprising a step of:
replacing said light source;
running said operation unit when replacing said light source; and
determining a replacement timing of said optical element based on a light amount of said light detected by said light detector when said operation receiving unit accepts a reset operation at said operation unit.

4. The replacement timing determination method, of said optical element according to claim 3, wherein:
said step of determining said replacement timing determines that said optical element is in said replacement timing of said optical element when said light amount of said light detected by said light detector when replacing said light source meets less than a threshold value when replacing said light source.

5. The replacement timing determination method, of an optical element, according to claim 3, further comprising a step of:
predicting said light amount of said light detected by said light detector at a next replacement timing of said light source when replacing said light source; wherein:
said step of determining said replacement timing determines that said optical element is in said replacement timing of said optical element when said light amount of said light detected by said light detector when replacing said light source meets less than said light amount that said step of predicting said light amount predicts.

6. A replacement timing determination method, of an optical element for an analysis system that comprises:
a light source that radiates light for an analysis;
an optical element that is operative for at least one of reflecting said light radiated from said light source and allowing said light to transmit therethrough; and
a light detector that detects at least one said light selected from a group consisting of a reflected light from said optical element and a transmitting light through said optical element, comprising a step of:
determining a replacement timing of said optical element based on a light amount of said light detected by said light detector when replacing said light source; and
predicting said light amount of said light detected by said light detector at a next replacement timing of said light source when replacing said light source; wherein:
said step of determining said replacement timing determines that said optical element is in said replacement timing of said optical element when said light amount of said light detected by said light detector when replacing said light source meets less than said light amount that said step of predicting said light amount predicts.

7. A replacement timing determination method of an optical element for an analysis system that comprises:
a light source that radiates light for an analysis;
an optical element that is operative for at least one of reflecting said light radiated from said light source and allowing said light to transmit therethrough;
a light detector that detects at least one said light selected from a group consisting of a reflected light from said optical element and a transmitting light through said optical element; and
a sensor that detects a replacement of said light source, comprising a step of:
replacing said light source;
detecting said replacement of said light source by said sensor; and
determining a replacement timing of said optical element based on a light amount of said light detected by said light detector when detecting said replacement.

* * * * *